United States Patent [19]

Drewlow

[11] Patent Number: Plant 6,494

[45] Date of Patent: Dec. 27, 1988

[54] STREPTOCARPUS PLANT NAMED ULYSSES

[75] Inventor: Lyndon W. Drewlow, Ashtabula, Ohio

[73] Assignee: Mikkelsens, Inc., Ashtabula, Ohio

[21] Appl. No.: 42,102

[22] Filed: Apr. 22, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Streptocarpus plant named Ulysses, characterized by its distinct deep violet blue flower color, highly floriferous and continuous flowering habits, ease of propagation and early flowering, and its ability to flower both under low light and high temperature conditions.

1 Drawing Sheet

The present invention relates to a new and distinctive cultivar of Streptocarpus plant, botanically known as *Streptocarpus×hybridus,* and known by the cultivar name Ulysses. Ulysses was developed by me in Ashtabula, Ohio through controlled breeding by crossing Mikkelsen Seedling 80-506-10 (seed parent)×Mikkelsen Seedling 82-1160-1 (pollen parent).

Asexual reproduction of Ulysses by leaf cuttings has shown that the unique features of this new Streptocarpus are stabilized and are reproduced true to type in successive propagations.

The following characteristics distinguish Ulysses from both its parent varieties and other cultivated Streptocarpus of this type known and used in the floriculture industry. Of the cultivars used for comparison purposes, Minerva, Ariadne, and Achilles are disclosed in pending applications of applicant.

1. Ulysses has a distinct deep violet purple flower with only the upper part of the throat having a light lavender purple color. Thor has a light lavender purple flower with white streaking coming out of the throat onto the lower petals, and Minerva has a dark blue flower color with cream streaking from the throat.

2. Flower size of Ulysses is larger than both Minerva and Thor, and similar in size to Ariadne and Achilles. Overlap of lobes of petals is greater in Ulysses than any of the other four cultivars.

3. Ulysses has a calyx that is purple in the bud stage and has a heavy purple cast on mature flowers, while Achilles has a purple calyx in the bud stage turning green on open flowers. Thor, Ariadne and Minerva have a green calyx both on buds and flowers.

4. The filament of Ulysses has a purple area about two-thirds of the way up, with Achilles having a red area in this same location. Thor and Minerva are white with a purple cast over the entire filament, while Ariadne has a pinkish cast.

5. Ulysses has a green with purple cast ovary, the style is white with purple hairs, and there is a heavy purple cast to the stigma; all the other cultivars mentioned have purple ovaries, and white styles and stigmas except Achilles, which has a light reddish purple cast to stigma.

6. Ulysses is similar to Achilles in plant height and spread. Ariadne is slightly more compact, and Minerva and Thor still more compact.

7. Ulysses is very floriferous due to the large number of flower stalks produced per leaf axil and the average of four blooms per flower stalk. Ulysses is similar in flowering habit to Achilles, with Ariadne, Thor and Minerva having more compact flower stalks.

8. Leaves of Ulysses are similar to Achilles, with Thor, Ariadne and Minerva having narrower leaves slightly shorter in length.

9. Ulysses propagates very well from a leaf cutting, producing numerous plantlets in 8 to 10 weeks depending on the time of year. Ulysses is early to flower when compared to older cultivars; from a well rooted plant from a 72 cell pack a well developed flowering plant is obtained in 6 to 10 weeks in a 10 cm pot.

10. Ulysses has shown the ability to flower both under the lower light conditions of winter (December to February) and under high temperatures of summer (July to September) without going out of bloom under greenhouse conditions.

The accompanying color photographs illustrate the overall appearance and flower color of Ulysses as closely as possible. The top photograph is entirely in color and comprises a perspective view of the plant. However, the depicted flower color is not precise. The bottom photograph is an enlarged black and white, with certain flowers being colored to accurately show the true flower color.

The following is a detailed description of Ulysses based on plants produced under commercial practices in the greenhouses of Mikkelsens Inc., Ashtabula, Ohio. Color references are made to The Royal Horticultural Society Colour Chart (RHS), except where general colors of ordinary dictionary significance are used.

Parentage: Controlled cross between Mikkelsen seedling 80-506-10 and Mikkelsen seedling 82-1160-1.

Propagation:

A. *Type cutting.*—Leaf.

B. *Time to develop plantlets.*—Summer: 8 weeks at 20° C. Winter: 10 weeks at 20° C.

C. *Rooting habit.*—Numerous, fine, fibrous.

Plant description:

A. *Form.*—Leaves rosette from a crown at the soil line with flower stalks forming at the leaf midrib. Many leaves in a symmetrical pattern with flowers carried well above foliage.

B. *Habit of growth.*—Vigorous, very free flowering, never going out of bloom once it starts blooming under greenhouse conditions. Several flowering stalks per leaf midrib.

C. *Height from soil line.*—20 to 25 cm at maturity in 10 cm pot to top of flowers.

D. *Spread.*—45 to 55 cm at maturity. Leaf size: 15 to 20 cm long and 8 to 10 cm wide at the widest point; leaf size can vary greatly with cultural conditions. Quantity: Mature plant can have more than 10 leaves. Leaf shape: Elliptical. Texture: Lower surface rugose with veins protruding and pubescent; upper surface rugose and pubescent. Margin: Crenate. Color: Young foliage top side 137C; under side 147D. Mature foliage top side 137A; under side 146D is close but there is more green in leaf but not as much as 137C. Ribs and veins: Pinnate. Rib and vein color: 146B. Leaf tips: Obtuse. Leaf base: Acute.

Flowering description: Flowers open one at a time on the individual flower spikes.

A. *Fully expanded.*—50 to 55 mm.

B. *Stem.*—Single, green with purplish tint; long, slightly pubescent and round, with several from a leaf midrib.

C. *Form.*—Funnel shaped with upper two petals reflexed and lower petals flattened to give an overall flat appearance.

D. *Flower bud description.*—20 to 25 cm at maturity, tubular with the end larger in diameter; 5 purple calyx folded over basal end.

E. *Flowers borne.*—In clusters of 3 to 6 flowers per flower stalk, with 4 the most common carried well above foliage. Pedicels of the flower in a single inflorescence vary in length.

F. *Quantity of flowers.*—Mature plant can have more than 15 flower stalks open at one time, with up to 6 flowers each.

G. *Permanence.*—Long lasting, 10 days or longer.

Color:

A. *Tonality from a distance.*—Violet purple with upper part of the throat being lavender purple in color.

B. *Upper surface of petals.*—There is not a precise color on RHS color chart. The true color is deeper than 86A but not as deep as 79A. The bottom photograph very accurately depicts true flower color.

C. *Reverse of petals.*—80B.

D. *Throat.*—Same as upper surface of petals except some 87B on the upper petals.

E. *Discoloration.*—Becomes slightly lighter purple in color.

Petals:

A. *Texture.*—Satin.

B. *Appearance.*—Individually lobed with slight crenate margins; top 2 petals are reflexed and smaller than the 3 bottom petals which are flat. Lobes slightly overlapped.

C. *Arrangement.*—Regularly united into an almost circular shape.

D. *Persistence.*—10 days or longer; petals remain on plant in dry form until picked.

E. *Fragrance.*—None.

Reproductive organs:

A. *Stamens.*—2 fertile, 2 sterile — very small. Anther shape: 2 fertile; interconnected and flat. Anther color: Purple. Filament: White with faint purple cast except for an area about ⅔ of the way up that is purple for about 2 mm; the white with purple cast then continues to the anther. Pollen color: Cream.

B. *Pistils.*—Stigma shape: 2 lobed flattened, rounded at end of lobes. Stigma color: Purple. Stigma size: 2 mm. Style color: White with fine purple hairs. Style size: 9 mm. Ovaries: Numerous, 15–17 mm on a receptive pistil, green with purple cast.

Disease resistance: No disease problems observed to date.

OTHER IMPORTANT CHARACTERISTICS

1. Compact growth habit with pliable leaves, making it good for 10 cm pot production and shipping.
2. Leaves do not scorch under high light.
3. Leaves do not spot with cold water (40° F.).
4. Early to flower from leaf propagation.

I claim:

1. A new and distinct Streptocarpus plant named Ulysses, as illustrated and described, and particularly characterized by its distinct deep violet blue flower color, highly floriferous and continuous flowering habits, ease of propagation and early flowering, and its ability to flower both under low light and high temperature conditions.

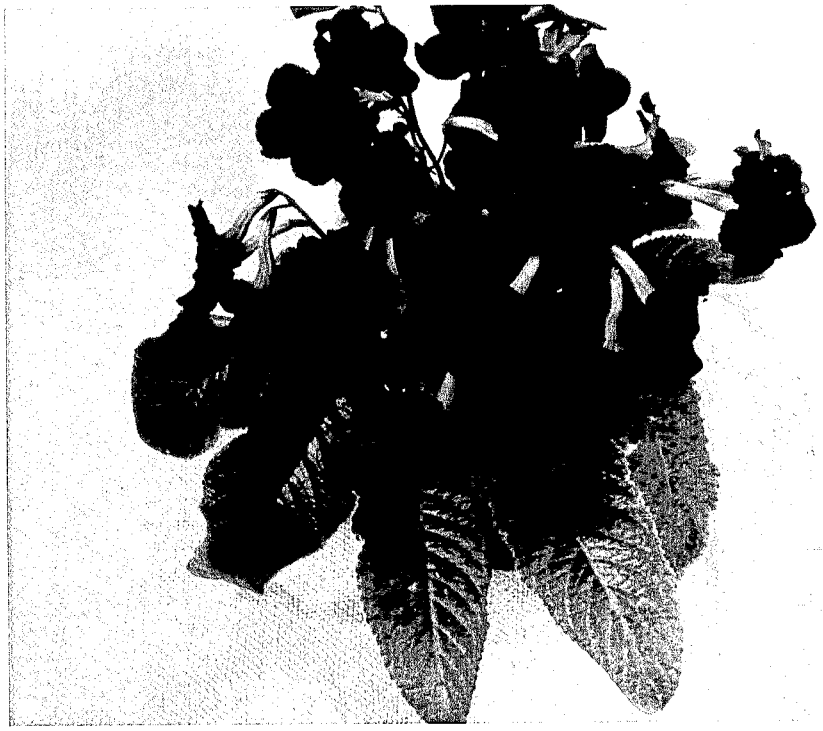
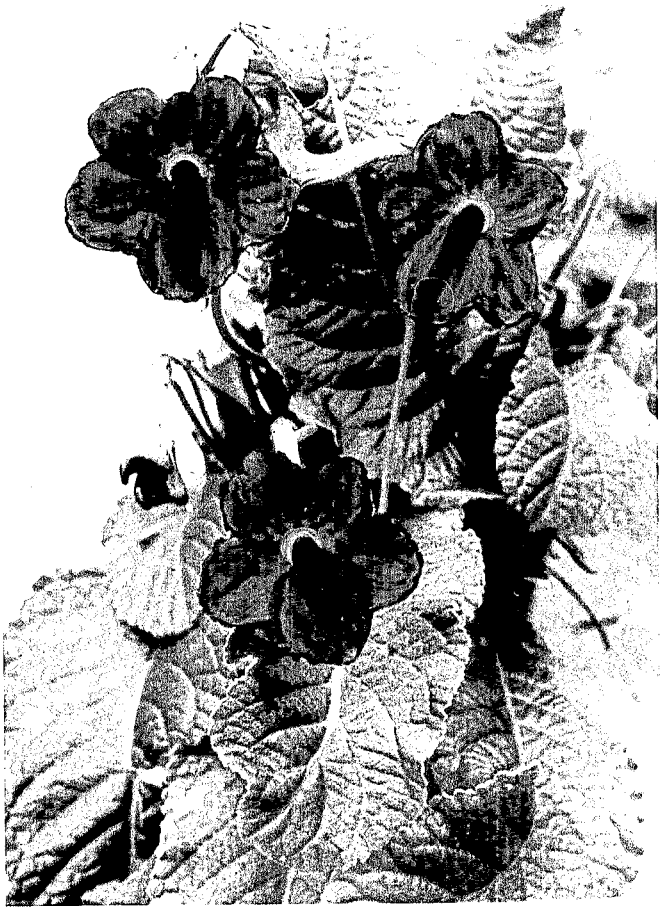

* * * * *